US009862869B2

(12) United States Patent
Hoffmann et al.

(10) Patent No.: US 9,862,869 B2
(45) Date of Patent: Jan. 9, 2018

(54) SILOXANE MIXTURES

(71) Applicant: Wacker Chemie AG, Munich (DE)

(72) Inventors: Florian Hoffmann, Munich (DE); Juergen Stohrer, Pullach (DE)

(73) Assignee: Wacker Chemie AG, Munich (DE)

( * ) Notice: Subject to any disclaimer, the term of this patent is extended or adjusted under 35 U.S.C. 154(b) by 491 days.

(21) Appl. No.: 14/409,341

(22) PCT Filed: Jun. 11, 2013

(86) PCT No.: PCT/EP2013/062037
§ 371 (c)(1),
(2) Date: Dec. 18, 2014

(87) PCT Pub. No.: WO2014/001081
PCT Pub. Date: Jan. 3, 2014

(65) Prior Publication Data
US 2015/0175868 A1  Jun. 25, 2015

(30) Foreign Application Priority Data

Jun. 29, 2012  (DE) .................. 10 2012 211 258

(51) Int. Cl.
| | | |
|---|---|---|
| C08L 83/04 | (2006.01) | |
| C09K 5/10 | (2006.01) | |
| C07F 7/21 | (2006.01) | |
| C07F 7/08 | (2006.01) | |
| F24J 2/46 | (2006.01) | |
| C08G 77/04 | (2006.01) | |

(52) U.S. Cl.
CPC .............. C09K 5/10 (2013.01); C07F 7/0849 (2013.01); C07F 7/21 (2013.01); C08L 83/04 (2013.01); F24J 2/4649 (2013.01); C08G 77/04 (2013.01); C08G 77/045 (2013.01)

(58) Field of Classification Search
CPC .............. C08L 83/04; C08G 77/04; C07F 7/21
See application file for complete search history.

(56) References Cited

U.S. PATENT DOCUMENTS

| | | | | |
|---|---|---|---|---|
| 3,694,405 A | * | 9/1972 | Litteral ...................... | C07F 7/21 521/33 |
| 4,122,109 A | | 10/1978 | Halm | |
| 4,193,885 A | | 3/1980 | Halm | |
| 4,222,952 A | * | 9/1980 | Vick ...................... | C08G 77/10 502/159 |
| 4,593,114 A | * | 6/1986 | Lewis ...................... | C07F 7/0874 556/450 |
| 2004/0144931 A1 | | 7/2004 | Harris | |

FOREIGN PATENT DOCUMENTS

| | | |
|---|---|---|
| CA | 2003332 | 5/1990 |
| DE | 2754705 A1 | 6/1978 |
| DE | 3839333 A1 | 5/1990 |
| EP | 1473346 B1 | 5/2006 |

OTHER PUBLICATIONS

"SYLTHERM 800 Heat Transfer Fluid—Product Technical Data", Brochure from the Dow Chemical Company, Oct. 1997.
PatBase Abstract for DE2754705.
International Search Report for PCT/EP2013/062037 dated Sep. 27, 2013.
Bannister et al. (1981). Studies of cyclic and linear poly (dimethyl siloxanes): 6. Effect of heat. Polymer, 22(3), 377-381.
Camino et al. (2001). Polydimethylsiloxane thermal degradation. Part 1. Kinetic aspects. Polymer, 42(6), 2395-2402.
Camino et al. (2002). Thermal polydimethylsiloxane degradation. Part 2. The degradation mechanisms. Polymer, 43 (7), 2011-2015.
Dow Corning. (1985). SYLTHERM 800 Heat Transfer Fluid. Witco Chemical Corporation, Golden Bear Refinery, Oildale, CA. Case History. 1-2.
Dow Corning. (1987). Silicone Ends Fouling in Heat-Transfer System. Arco Oil and Gas Company, Gulf of Mexico. Case History. 1-2.
Dow Corning. (1987). SYLTHERM 800 Heat Transfer Liquid. Texas Oil and Gas, Tonkawa Gas Processing Facility, Grapeland, TX. Case History. 1-2.
Dow Corning. (1987). Equipment Manufacturer Reduces Downtime with Silicone Fluid. Artisan Industries, Inc., Waltham, MA. Case History. 1-2.
Dow Corning. (1987). High-Temperature Heat Transfer Fluid Saves in Equipment Costs for DuPont. DuPont Automotive Finishes, Front Royal, VA. Case History. 1-2.

(Continued)

*Primary Examiner* — Margaret G Moore
(74) *Attorney, Agent, or Firm* — Caesar Rivise, PC

(57) ABSTRACT

The invention provides mixtures, liquid at 25° C., of methylpolysiloxanes comprising at least two methylpolysiloxanes selected from linear compounds of the general formula I $Me_3SiO\text{-}(Me_2SiO)x\text{-}SiMe_3$ (I), and cyclic compounds of the general formula II $(Me_2SiO)y$ (II), wherein the mixture comprises at least one linear methylpolysiloxane of the general formula I and at least one cyclic methylpolysiloxane of the general formula II, Me means methyl radical, x has values greater than or equal to zero and the arithmetic mean of x, weighted by the molar proportions, over all linear methylpolysiloxanes is between 3 and 20, y has values greater than or equal to 3 and the arithmetic mean of y, weighted by the molar proportions, over all cyclic methylpolysiloxanes is between 3 and 6, the numerical ratio of the $Me_3Si$— chain ends groups in the compounds of the general formula I to the sum of the $Me_2SiO$— units in the compounds of the general formulae I and II is at least 1:2 and at most 1:10, and further definitions are described in claim 1, and the use of the mixtures as heat carrier fluids.

11 Claims, No Drawings

(56) References Cited

OTHER PUBLICATIONS

Dow Corning. (1987). Silicone Fluid Improves Laboratory Environment. Blaw-Knox Food and Chemical Company, Buffalo, NY. Case History. 1-2.
Dow Corning. (1988). Resource Recovery Plant Uses Silicone Fluid for Petrecology. Evergreen Oil, Newark, CA. Case History. 1-2.
Plataforma Solar De Almeria. (2015). Annual Report 2015. Goberno de Espana. 1-163.
Thomas et al. (1969). Thermal analysis of polydimethylsiloxanes. I. Thermal degradation in controlled atmospheres. Journal of Polymer Science Part A-2: Polymer Physics, 7(3), 537-549.
Zeldin et al. (1983). Mechanism of thermal depolymerization of trimethylsiloxy-terminated polydimethylsiloxane. Journal of Polymer Science: Polymer Chemistry Edition, 21(5), 1361-1369.

\* cited by examiner

SILOXANE MIXTURES

BACKGROUND OF THE INVENTION

The present invention relates to mixtures of siloxanes and to the use thereof as heat transfer fluid.

Organosiloxanes and organopolysiloxanes (silicone oils), referred to collectively hereinafter as "siloxanes" for short, frequently find use as heat transfer fluids because of their high thermal stability and wide liquid range and the low degree to which their viscosity depends on temperature. DE 2754705 A1 details the advantages of siloxanes over other heat transfer agents. Especially within the range of very low (below −50° C.) or very high temperatures (200-400° C.), they are superior to organic heat transfer fluids or are the only nonionic heat transfer fluid that is usable at all. For example, EP 1473346 B1 describes mixtures of linear and cyclic dimethylpolysiloxanes usable as coolants down to −100° C. In addition, the brochure "SYLTHERM 800 Heat Transfer Fluid—Product Technical Data" from The Dow Chemical Company (CH 153-046-E-1097, October 1997) describes a linear, permethylated silicone oil ("Syltherm 800") and states the maximum prolonged use temperature as 400° C. (closed system with exclusion of air). It is also stated there that, in the case of brief thermal stress, up to 538° C. is attainable without substantial breakdown.

These properties of the siloxanes make them ideal for use as high-temperature heat transfer fluids, for example in solar thermal power plants, especially in those with parabolic trough and Fresnel technology, where the heat transfer fluid is subjected to high thermal stress up to 400° C. and severe temperature variations for a number of years. The use of silicone oils in solar thermal devices is described in DE 2754705 A1, U.S. Pat. No. 4,122,109 and U.S. Pat. No. 4,193,885.

The composition of siloxane mixtures is temperature-dependent by virtue of rearrangement processes, and as a result is also time-dependent until attainment of the equilibrium state at the chosen temperature. In the case of linear, permethylated silicone oils, the attainment of the equilibrium state at 400° C., for example, can take a few days. In parallel, there is thus also a change in the physical properties. The result of this can be that important operating parameters of a device operated with a siloxane mixture as heat transfer fluid, for example the vapor pressure or viscosity, change considerably with time. This is disadvantageous, since it can necessitate additional expenditure on control and regulation or even additional expenditure in the construction of the device, or the device may be usable only to a limited degree, if at all, within this period.

Patent specifications U.S. Pat. No. 4,122,109 and U.S. Pat. No. 4,193,885 describe the addition of metallic stabilizers and optionally of hydrogen-containing silicon compounds to noncyclic methylpolysiloxanes, in order to suppress the temperature-dependent change in the chemical composition and hence to keep the composition and the physical properties stable over time. However, it is clear from the examples that the rearrangements cannot be entirely suppressed. The abovementioned accompanying product brochure ("Syltherm 800") states that the rearrangement processes are slowed significantly but do take place, and the equilibrium state is ultimately attained after a few months. This is associated with a considerable rise in the vapor pressure. However, since heat transfer fluids, for reasons of cost, are used in solar thermal power plants for a number of years, addition of stabilizers is therefore unsuitable for this application, since it cannot in fact prevent the rearrangements over this period, and is actually disadvantageous as a result of the increase in material costs that it causes.

It is therefore an object of the invention to provide siloxanes which, after attainment of a particular temperature, have nearly constant physical properties over time, in order to avoid the disadvantages mentioned.

DESCRIPTION OF THE INVENTION

It has now been found that particular siloxane mixtures under thermal stress at a constant temperature can have nearly constant physical properties over time even though the chemical composition thereof changes with time up to the equilibrium state. Surprisingly, the composition of these siloxane mixtures need not correspond to the equilibrium composition at this temperature.

The invention provides mixtures of methylpolysiloxanes containing at least two methylpolysiloxanes selected from linear compounds of the general formula I $$Me_3SiO\text{-}(Me_2SiO)_x\text{---}SiMe_2 \quad (I)$$

and cyclic compounds of the general formula II $$(Me_2SiO)_y \quad (II)$$

where
the mixture contains at least one linear methylpolysiloxane of the general formula I and at least one cyclic methylpolysiloxane of the general formula II,
Me is a methyl radical,
x has values greater than or equal to zero and the arithmetic mean of x over all the linear methylpolysiloxanes, weighted by the molar proportions, is between 3 and 20,
y has values greater than or equal to 3 and the arithmetic mean of y over all the cyclic methylpolysiloxanes, weighted by the molar proportions, is between 3 and 6,
the numerical ratio of the Me₃Si— chain end groups in the compounds of the general formula I to the sum total of Me₂SiO— units in the compounds of the general formulae I and II is at least 1:2 and at most 1:10,
the proportions of the linear methylpolysiloxanes of the general formula I are each independently,
for x=zero, between zero and 14% by mass,
for x=1 to 3, in each case between zero and 14% by mass,
for x=4 and 5, in each case between zero and 14% by mass,
for x=6 to 9, in each case between zero and 16% by mass,
for x=10 and 11, in each case between zero and 12% by mass,
for x=12 to 14, in each case between zero and 10% by mass,
for x=15 to 28, in each case between zero and 10% by mass,
for x=29 and 30, in each case between zero and 8% by mass,
for x=31 to 34, in each case between zero and 4% by mass,
for x=35 to 40, in each case between zero and 2% by mass,
for x=41 to 70, in each case between zero and 1% by mass,
and,
for x greater than 70, in each case between zero and 0.5% by mass,
the proportions of the cyclic methylpolysiloxanes of the general formula II are each independently, for y=3, between zero and 10% by mass,
for y=4, between zero and 30% by mass,
for y=5, between zero and 15% by mass,
for y=6, between zero and 10% by mass,
for y=7, between zero and 8% by mass,
for y=8 to 11, in each case between zero and 5% by mass,
for y=12 to 15, in each case between zero and 2.5% by mass,
for y=16 to 19, in each case between zero and 2% by mass,
for y=20 to 40, in each case between zero and 1% by mass,
and,
for y greater than 40, in each case between zero and 0.5% by mass,
the sum of the proportions of all the cyclic methylpolysiloxanes of the general formula II is at least 10% by mass and at most 40% by mass, and
the mixture is liquid at 25° C. and has a viscosity of less than 100 mPa*s.

The composition of the mixture is selected such that at least one of the physical properties of density, vapor pressure, viscosity, heat capacity or thermal conductivity remains nearly constant over time at a constant temperature during thermal stress on the mixture. The composition of the mixture can, if the desired physical properties of all the components of the mixture are known as a function of temperature, be determined by calculation or else empirically. The case that the composition of the mixture corresponds to the equilibrium mixture at the chosen temperature is trivial. The invention is based on the ability of mixtures of different composition than the equilibrium composition also to have the physical properties of the equilibrium mixture at the chosen temperature.

The inventive siloxane mixtures have the advantage that at least one physical property selected from density, vapor pressure, viscosity, heat capacity and thermal conductivity can be kept constant over time, even though the chemical composition of the siloxane mixture is still changing until attainment of the equilibrium state. In the construction and operation of the solar thermal device, there is therefore no need to take account of any changes in the selected physical properties.

The variable x preferably assumes values between zero and 100, more preferably between zero and 70, most preferably between zero and 40. The arithmetic mean of x over all the linear methylpolysiloxanes, weighted by the molar proportions, is preferably between 4 and 15, more preferably between 5 and 10, including the limits stated in each case.

The variable y preferably assumes values between 3 and 100, more preferably between 3 and 70, most preferably between 3 and 40. The arithmetic mean of y over all the cyclic methylpolysiloxanes, weighted by the molar proportions, is preferably between 3.5 and 5.5, more preferably between 4 and 5, especially between 4 and 4.5, including the limits stated in each case.

The numerical ratio of the $Me_3Si$— chain end groups in the general formula I to the sum total of $Me_2SiO$— units in the general formulae I and II is preferably at least 1:2.5 and at most 1:8, more preferably at least 1:3 and at most 1:6.

The proportions of the linear methylpolysiloxanes of the general formula I are preferably each independently,
for x=zero, between 0.1 and 12% by mass,
for x=1 to 3, in each case between zero and 11% by mass,
for x=4 and 5, in each case between 1 and 11% by mass,
for x=6 to 9, in each case between 1 and 14% by mass,
for x=10 and 11, in each case between 1 and 10% by mass,
for x=12 to 14, in each case between 0.5 and 7.5% by mass,
for x=15 to 28, in each case between 0.1 and 7.5% by mass,
for x=29 and 30, in each case between 0.1 and 6% by mass,
for x=31 to 34, in each case between zero and 3% by mass,
for x=35 to 40, in each case between zero and 1.5% by mass,
for x=41 to 70, in each case between zero and 0.5% by mass,
and,
for x greater than 70, in each case between zero and 0.1% by mass,
and more preferably each independently,
for x=zero, between 0.5 and 10% by mass,
for x=1 to 3, in each case between zero and 8% by mass,
for x=4 and 5, in each case between 1.5 and 8% by mass,
for x=6 to 9, in each case between 1.5 and 12% by mass,
for x=10 and 11, in each case between 1.5 and 8% by mass,
for x=12 to 14, in each case between 1 and 5% by mass,
for x=15 to 28, in each case between 0.2 and 5% by mass,
for x=29 and 30, in each case between 0.1 and 4% by mass,
for x=31 to 34, in each case between zero and 2% by mass,
for x=35 to 40, in each case between zero and 1% by mass,
for x=41 to 70, in each case between zero and 0.1% by mass,
and,
for x greater than 70, in each case zero % by mass.

The proportions of the cyclic methylpolysiloxanes of the general formula II are preferably each independently,
for y=3, between zero and 7.5% by mass,
for y=4, between zero and 25% by mass,
for y=5, between zero and 12.5% by mass,
for y=6, between zero and 7.5% by mass,
for y=7, between zero and 6% by mass,
for y=8 to 11, in each case between zero and 3.5% by mass,
for y=12 to 15, in each case between zero and 2% by mass,
for y=16 to 19, in each case between zero and 1.5% by mass,
for y=20 to 40, in each case between zero and 0.8% by mass,
and,
for y greater than 40, in each case between zero and 0.2% by mass,
and more preferably each independently,
for y=3, between zero and 5% by mass,
for y=4, between zero and 20% by mass,
for y=5, between zero and 10% by mass,
for y=6, between zero and 5% by mass,
for y=7, between zero and 4% by mass,
for y=8 to 11, in each case between zero and 2% by mass,
for y=12 to 15, in each case between zero and 1.5% by mass,
for y=16 to 19, in each case between zero and 1% by mass,
for y=20 to 40, in each case between zero and 0.5% by mass,
and
for y greater than 40, in each case zero % by mass.

Preferably, the sum total of the proportions of all the cyclic methylpolysiloxanes of the general formula II is at least 12.5% by mass and at most 35% by mass, especially at least 15% by mass and at most 30% by mass.

The viscosity of the inventive siloxane mixtures at 25° C. preferably has values below 50 mPa*s, more preferably below 20 mPa*s, most preferably below 10 mPa*s.

The inventive siloxane mixtures may be in a monomodal, bimodal or multimodal molar mass distribution; at the same time, the molar mass distribution may be narrow or broad. Preferably, the inventive siloxane mixtures have a bimodal, trimodal or tetramodal molar mass distribution.

The inventive siloxane mixtures preferably contain less than 1000 ppm of water, more preferably less than 500 ppm of water, most preferably less than 200 ppm of water, based in each case on the mass.

In a preferred embodiment, the inventive mixtures of methylpolysiloxanes consist of 1-10% by mass of linear methylpolysiloxanes of the general formula I in which x assumes values between zero and 8 and the arithmetic mean of x, weighted by the molar proportions, is between zero and 1.5, 15-30% by mass of cyclic methylpolysiloxanes of the general formula II in which y assumes values between 3 and 12 and the arithmetic mean of y, weighted by the molar proportions, is between 3.5 and 5, and 60-84% by mass of linear methylpolysiloxanes of the general formula I in which x assumes values between 4 and 70 and the arithmetic mean of x, weighted by the molar proportions, is between 4 and 15, including the limits stated in each case, where the mixtures have a trimodal molar mass distribution and a viscosity at 25° C. of less than 10 mPa*s.

Preferably, the physical properties, selected from density, vapor pressure, viscosity, heat capacity and thermal conductivity of the mixture, especially all these properties, after attainment of a constant temperature between 300° C. and 600° C. under exclusion of air, change by not more than 15%, preferably not more than 10%, more preferably not more than 5%, before attainment of the equilibrium composition.

Inventive siloxane mixtures can be prepared by formulating or mixing pure siloxanes of the general formulae I or II or any desired mixtures of such siloxanes in any sequence, or metering one into another, optionally also with multiple repetitions, and optionally also alternately or simultaneously. By means of suitable processes, for example distillation, siloxanes or siloxane mixtures can also be removed again. The composition of the inventive siloxane mixture is controlled via the amounts of siloxanes of the general formulae I and II used or removed.

The process can be conducted at room temperature and ambient pressure, but also at elevated or reduced temperature and elevated or reduced pressure.

Inventive siloxane mixtures can additionally be prepared by hydrolyzing or co-hydrolyzing suitable chlorosilanes, alkoxysilanes or mixtures of chlorosilanes or alkoxysilanes, and then freeing them of by-products such as hydrogen chloride or alcohols and optionally of excess water. Optionally, further siloxane can be added to the siloxane mixture obtained, or it can be removed by suitable processes, for example distillation. The process can be conducted at room temperature and ambient pressure, but also at elevated or reduced temperature and elevated or reduced pressure. The composition of the inventive siloxane mixture is controlled via the ratio of the amounts of silanes and/or siloxanes used and of any amounts removed again.

Inventive siloxane mixtures can also be prepared by heating pure siloxanes of the general formulae I or II or any desired mixtures of such siloxanes to temperatures at which the rearrangement processes mentioned take place, such that siloxane mixtures with altered composition are obtained. This composition may, but need not, correspond to the equilibrium composition at this temperature. The heating can take place in an open or closed system, preferably under a protective gas atmosphere. The process can be conducted at ambient pressure, but also at elevated or reduced pressure. The heating can take place without catalysis or in the presence of a homogeneous or heterogeneous catalyst, for example an acid or base. Thereafter, the catalyst can, but need not, be deactivated or removed from the siloxane mixture, for example by distillation or filtration. By means of suitable processes, for example distillation, it is also possible to remove siloxanes or siloxane mixtures again. The composition of the inventive siloxane mixture is controlled via the ratio of the amounts of siloxanes of the general formulae I and II used and of any amounts removed again, the temperature and method (open or closed system) and duration of heating.

The three processes described above can also be combined. They can optionally be conducted in the presence of one or more solvents. Preference is given to using no solvent. The silanes, silane mixtures, siloxanes and siloxane mixtures used are either standard products in the silicone industry or can be prepared by synthesis methods known from the literature.

The inventive siloxane mixtures may comprise dissolved or suspended or emulsified additives, in order to increase the stability thereof or influence the physical properties thereof. Dissolved metal compounds, for example iron carboxylates, as free-radical scavengers and oxidation inhibitors can increase the service life of a heat transfer agent. Suspended additives, for example carbon or iron oxide, can improve physical properties of a heat transfer agent, for example heat capacity or thermal conductivity.

Preferably, the sum total of the proportions of all the methylpolysiloxanes of the general formulae I or II is at least 95% by mass, particularly at least 98% by mass, especially at least 99.5% by mass, based on the overall mixture.

The inventive siloxane mixtures can be used as heat transfer fluids, preferably as high-temperature heat transfer agents in solar thermal devices, especially in parabolic trough and Fresnel power plants. They can additionally be used as heat transfer fluids in the chemical industry and in the metals industry, as heat transfer fluids for low temperatures and as working fluids in thermal engines, especially of the solar thermal type. The siloxane mixtures are preferably used at temperatures of 200° C. to 550° C., more preferably 300° C. to 500° C., especially 350° C. to 450° C. At temperatures above 200° C., use under a protective gas atmosphere is preferable in order to avoid oxidative breakdown.

EXAMPLES

Example 1

Comparative Example (Noninventive)

151 g of a Wacker AK 5 silicone oil (mixture of linear methylpolysiloxanes of the general formula I having an arithmetic mean, weighted by the molar proportions, of x=8.2 ($^{29}$Si NMR), corresponding to 10.2 repeat units including the two trimethylsilyl chain end groups or an average of 10.2 silicon atoms per molecule; consisting of (each in GC area %): 0.03% Me$_3$SiO-(Me$_2$SiO)$_2$—SiMe$_3$, 0.65% Me$_3$SiO-(Me$_2$SiO)$_3$—SiMe$_3$, 4.0% Me$_3$SiO-(Me$_2$SiO)$_4$—SiMe$_3$, 9.2% Me$_3$SiO-(Me$_2$SiO)$_5$—SiMe$_3$, 12.6% Me$_3$SiO-(Me$_2$SiO)$_6$—SiMe$_3$, 13.0% Me$_3$SiO-(Me$_2$SiO)$_7$—SiMe$_3$, 11.8% Me$_3$SiO-(Me$_2$SiO)$_8$—SiMe$_3$, 9.9% Me$_3$SiO-(Me$_2$SiO)$_9$—SiMe$_2$, 8.1% Me$_3$SiO-(Me$_2$SiO)$_{10}$—SiMe$_3$, 6.5% Me$_3$SiO-(Me$_2$SiO)$_{11}$—SiMe$_3$, 5.1% Me$_3$SiO-(Me$_2$SiO)$_{12}$—SiMe$_3$, 19.0% Me$_3$SiO-(Me$_2$SiO)$_x$—SiMe$_2$ with x>12, 0.12% cyclic methylpolysiloxanes of the general formula II with y=5 to 12; viscosity 5.4 mPa*s) are heated to internal temperature 405° C. in an autoclave with a pressure transducer for 1 week. The vapor pressure/time curve recorded in Table 1 shows that a nearly constant pressure of ~16 bar is not achieved until after ~5 days. Thereafter, the silicone oil has the following composition (each in GC area %):

1.4% Me$_2$Si—O—SiMe$_2$, 2.5% Me$_3$SiO-Me$_2$SiO—SiMe$_3$, 3.5% Me$_3$SiO-(Me$_2$SiO)$_2$—SiMe$_3$, 4.3% Me$_3$SiO-(Me$_2$SiO)$_3$—SiMe$_3$, 5.5% Me$_3$SiO-(Me$_2$SiO)$_4$—SiMe$_3$, 6.9% Me$_3$SiO-(Me$_2$SiO)$_5$—SiMe$_3$, 7.7% Me$_3$SiO-(Me$_2$SiO)$_6$—SiMe$_3$, 7.4% Me$_3$SiO-(Me$_2$SiO)$_7$—SiMe$_3$, 6.5% Me$_3$SiO-(Me$_2$SiO)$_8$—SiMe$_3$, 5.5% Me$_3$SiO-(Me$_2$SiO)$_9$—SiMe$_3$, 4.6% Me$_3$SiO-(Me$_2$SiO)$_{10}$—SiMe$_3$, 3.8% Me$_3$SiO-(Me$_2$SiO)$_{11}$—SiMe$_3$, 3.2% Me$_3$SiO-(Me$_2$SiO)$_{12}$—SiMe$_3$, 20.2% Me$_3$SiO-(Me$_2$SiO)$_x$—SiMe$_3$ with x>12, 1.8% (Me$_2$SiO)$_3$, 10.1% (Me$_2$SiO)$_4$, 3.6% (Me$_2$SiO)$_5$, 0.9% (Me$_2$SiO)$_6$, 0.3% (Me$_2$SiO)$_7$, 0.3% (Me$_2$SiO)$_y$, with y>7; arithmetic mean, weighted by the molar proportions, of x=7.6 ($^{29}$Si NMR); viscosity 4.6 mPa*s.

Example 2

Siloxane Mixture with Constant Vapor Pressure 150 g of a mixture of 80% by mass of Wacker AK 5 silicone oil (for composition see example 1), 16% by mass of octamethylcyclotetrasiloxane and 4% by mass of hexamethyldisiloxane (calculated composition: 4.0% Me$_3$Si—O—SiMe$_3$, 0.02% Me$_3$SiO-(Me$_2$SiO)$_2$—SiMe$_3$, 0.52% Me$_3$SiO-(Me$_2$SiO)$_3$—SiMe$_3$, 3.2% Me$_3$SiO-(Me$_2$SiO)$_4$—SiMe$_3$, 7.4% Me$_3$SiO-(Me$_2$SiO)$_5$—SiMe$_3$, 10.1% Me$_3$SiO-(Me$_2$SiO)$_6$—SiMe$_3$, 10.4% Me$_3$SiO-(Me$_2$SiO)$_7$—SiMe$_3$, 9.4% Me$_3$SiO-(Me$_2$SiO)$_8$—SiMe$_3$, 7.9% Me$_3$SiO-(Me$_2$SiO)$_9$—SiMe$_3$, 6.5% Me$_3$SiO-(Me$_2$SiO)$_{10}$—SiMe$_3$, 5.2% Me$_3$SiO-(Me$_2$SiO)$_{11}$—SiMe$_3$, 4.1% Me$_3$SiO-(Me$_2$SiO)$_{12}$—SiMe$_3$, 15.2% Me$_3$SiO-(Me$_2$SiO)$_x$—SiMe$_3$ with x>12, 16.0% (Me$_2$SiO)$_4$, 0.10% cyclic methylpolysiloxanes of the general formula II with y=5 to 12; viscosity 4.6 mPa*s) are heated to internal temperature 400° C. in an autoclave with a pressure transducer for 1 week. The vapor pressure/time curve recorded in table 1 shows that, immediately after attainment of 400° C., a nearly constant pressure of ~17 bar is attained. Thereafter, the silicone oil has the following composition (each in GC area %):

4.6% Me$_3$Si—O—SiMe$_3$, 1.9% Me$_3$SiO-Me$_2$SiO—SiMe$_3$, 2.7% Me$_3$SiO-(Me$_2$SiO)$_2$—SiMe$_3$, 3.4% Me$_3$SiO-(Me$_2$SiO)$_3$—SiMe$_3$, 4.4% Me$_3$SiO-(Me$_2$SiO)$_4$—SiMe$_3$, 5.8% Me$_3$SiO-(Me$_2$SiO)$_5$—SiMe$_3$, 6.8% Me$_3$SiO-(Me$_2$SiO)$_6$—SiMe$_3$, 6.7% Me$_3$SiO-(Me$_2$SiO)$_7$—SiMe$_3$, 6.0% Me$_3$SiO-(Me$_2$SiO)$_8$—SiMe$_3$, 5.1% Me$_3$SiO-(Me$_2$SiO)$_9$—SiMe$_3$, 4.4% Me$_3$SiO-(Me$_2$SiO)$_{10}$—SiMe$_3$, 3.7% Me$_3$SiO-(Me$_2$SiO)$_{11}$—SiMe$_3$, 3.2% Me$_3$SiO-(Me$_2$SiO)$_{12}$—SiMe$_3$, 21.7% Me$_3$SiO-(Me$_2$SiO)$_x$—SiMe$_3$ with x>12, 1.9% (Me$_2$SiO)$_3$, 11.7% (Me$_2$SiO)$_4$, 4.3% (Me$_2$SiO)$_5$, 1.1% (Me$_2$SiO)$_6$, 0.3% (Me$_2$SiO)$_7$, 0.3% (Me$_2$SiO)$_y$, with y>7; arithmetic mean, weighted by the molar proportions, of x=8.6 ($^{29}$Si NMR); viscosity 4.8 mPa*s.

TABLE 1

| Time [h] | Ex. 1* pressure [bar] | Ex. 2 pressure [bar] | Time [h] | Ex. 1* pressure [bar] | Ex. 2 pressure [bar] |
|---|---|---|---|---|---|
| 0 | 5.8 | 16.2 | 24 | 12.0 | 16.4 |
| 1 | 6.5 | 17.3 | 36 | 13.2 | 16.7 |
| 2 | 7.2 | 17.4 | 48 | 13.7 | 16.7 |
| 3 | 7.7 | 17.1 | 60 | 14.3 | 17.0 |
| 4 | 8.1 | 17.0 | 72 | 14.4 | 17.2 |
| 5 | 8.5 | 17.2 | 84 | 14.8 | 16.7 |
| 6 | 8.7 | 17.1 | 96 | 15.1 | 17.3 |
| 7 | 9.1 | 16.7 | 108 | 15.4 | 17.2 |
| 8 | 9.3 | 16.7 | 120 | 15.7 | 17.0 |
| 9 | 9.5 | 16.8 | 132 | 15.8 | 17.3 |
| 10 | 9.6 | 16.8 | 144 | 15.8 | 17.3 |
| 11 | 9.7 | 16.7 | 156 | 16.0 | 17.3 |
| 12 | 10.1 | 16.4 | 161 | 16.0 | 17.3 |
| 18 | 11.4 | 16.4 | 165 | 16.0 | — |

*non-inventive

Example 2 as compared with example 1 demonstrates the present invention: a suitably chosen siloxane mixture, at constant temperature, has a nearly constant physical property over time (in this case the vapor pressure), even though the chemical composition changes with time.

The invention claimed is:
1. A mixture of methylpolysiloxanes containing at least two methylpolysiloxanes selected from linear compounds of the general formula I

Me$_3$SiO-(Me$_2$SiO)$_x$—SiMe$_3$ (I)

and cyclic compounds of the general formula II

(Me$_2$SiO)$_y$ (II)

where
the mixture contains at least one linear methylpolysiloxane of the general formula I and at least one cyclic methylpolysiloxane of the general formula II,
Me is a methyl radical,
x has values greater than or equal to zero and an arithmetic mean of x over all the linear methylpolysiloxanes, weighted by molar proportions, is between 3 and 20,
y has values greater than or equal to 3 and an arithmetic mean of y over all the cyclic methylpolysiloxanes, weighted by molar proportions, is between 3 and 6,
a numerical ratio of Me$_3$Si— chain end groups in the compounds of the general formula I to a sum total of Me$_2$SiO— units in the compounds of the general formulae I and II is at least 1:2 and at most 1:10,
proportions of the linear methylpolysiloxanes of the general formula I are each independently,
for x=zero, between zero and 14% by mass,
for x=1 to 3, in each case between zero and 14% by mass,
for x=4 and 5, in each case between zero and 14% by mass,
for x=6 to 9, in each case between zero and 16% by mass,
for x=10 and 11, in each case between zero and 12% by mass,
for x=12 to 14, in each case between zero and 10% by mass,
for x=15 to 28, in each case between zero and 10% by mass, for x=29 and 30, in each case between zero and 8% by mass, for x=31 to 34, in each case between zero and 4% by mass, for x=35 to 40, in each case between zero and 2% by mass, for x=41 to 70, in each case between zero and 1% by mass, and, for x greater than 70, in each case between zero and 0.5% by mass, proportions of the cyclic methylpolysiloxanes of the general formula II are each independently, for y=3, between zero and 10% by mass, for y=4, between zero and 30% by mass, for y=5, between zero and 15% by mass, for y=6, between zero and 10% by mass, for y=7, between zero and 8% by mass, for y=8 to 11, in each case between zero and 5% by mass, for y=12 to 15, in each case between zero and 2.5% by mass, for y=16 to 19, in each case between zero and 2% by mass, for y=20 to 40, in each case between zero and 1% by mass, and, for y greater than 40, in each case between zero and 0.5% by mass, a sum of the proportions of all the cyclic methylpolysiloxanes of the general formula II is at least 10% by mass and at most 40% by mass, and wherein the mixture consists of 1-10% by mass of linear methylpolysiloxanes of the general formula I in which x assumes values between zero and 8 and the arithmetic mean of x, weighted by the molar proportions, is between zero and 1.5, and 15-30% by mass of cyclic methylpolysiloxanes of the general formula II in which y assumes values between 3 and 12 and the arithmetic mean of y, weighted by the molar proportions, is between 3.5 and 5, and 60-84% by mass of linear methylpolysiloxanes of the general formula I, in which x assumes values between 4 and 70 and the arithmetic mean of x, weighted by the molar proportions, is between 4 and 15, including the limits stated in each case, where the mixture has a viscosity at 25° C. of less than 10 mPa*s.

2. The mixture as claimed in claim 1, in which the arithmetic mean of x over all the linear methylpolysiloxanes, weighted by the molar proportions, is between 4 and 15.

3. The mixture as claimed in claim 1, in which the arithmetic mean of y over all the cyclic methylpolysiloxanes, weighted by the molar proportions, is between 3.5 and 5.5.

4. The mixture as claimed in claim 1, in which the numerical ratio of the $Me_3Si$— chain end groups in the compounds of the general formula I to the sum total of $Me_2SiO$— units in the compounds of the general formulae I and II is at least 1:2.5 and at most 1:8.

5. The mixture as claimed in claim 1, in which physical properties selected from density, vapor pressure, viscosity, heat capacity and thermal conductivity of the mixture, after attainment of a constant temperature between 300° C. and 600° C. under exclusion of air, change by not more than 15% before attainment of an equilibrium composition.

6. A method of transferring heat, said method comprising providing a mixture as claimed in claim 1 as a heat transfer fluid and heating the mixture to transfer heat.

7. The method as claimed in claim 6 for solar thermal devices.

8. The method as claimed in claim 6, wherein the mixture is heated to temperatures of 200° C. to 550° C.

9. The mixture as claimed in claim 2, in which the arithmetic mean of y over all the cyclic methylpolysiloxanes, weighted by the molar proportions, is between 3.5 and 5.5.

10. The mixture as claimed in claim 9, in which the numerical ratio of the $Me_3Si$— chain end groups in the compounds of the general formula I to the sum total of $Me_2SiO$— units in the compounds of the general formulae I and II is at least 1:2.5 and at most 1:8.

11. The mixture as claimed in claim 10, in which physical properties selected from density, vapor pressure, viscosity, heat capacity and thermal conductivity of the mixture, after attainment of a constant temperature between 300° C. and 600° C. under exclusion of air, change by not more than 15% before attainment of an equilibrium composition.

* * * * *